(12) United States Patent
Luo et al.

(10) Patent No.: US 11,472,768 B2
(45) Date of Patent: Oct. 18, 2022

(54) HPTS SERIES DERIVATIVES AND SYNTHESIS METHOD THEREFOR

(71) Applicant: NANJING UNIVERSITY, Nanjing (CN)

(72) Inventors: Jun Luo, Nanjing (CN); Xuan Hu, Nanjing (CN); Chaogen Liang, Nanjing (CN); Wen Fang, Nanjing (CN); Zhaodong Liu, Nanjing (CN); Daixia Yin, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 315 days.

(21) Appl. No.: 16/756,475

(22) PCT Filed: Nov. 19, 2018

(86) PCT No.: PCT/CN2018/116080
§ 371 (c)(1),
(2) Date: Apr. 16, 2020

(87) PCT Pub. No.: WO2019/242220
PCT Pub. Date: Dec. 26, 2019

(65) Prior Publication Data
US 2020/0299231 A1    Sep. 24, 2020

(30) Foreign Application Priority Data
Jun. 19, 2018  (CN) .......................... 201810629427.6

(51) Int. Cl.
*C07C 303/28* (2006.01)
*C07C 303/02* (2006.01)
(Continued)

(52) U.S. Cl.
CPC .......... *C07C 303/28* (2013.01); *C07C 303/02* (2013.01); *C07C 303/38* (2013.01);
(Continued)

(58) Field of Classification Search
None
See application file for complete search history.

(56) References Cited

U.S. PATENT DOCUMENTS

| | | | |
|---|---|---|---|
| 2003/0049714 A1* | 3/2003 | Conrad | ................ C09B 57/001 |
| | | | 558/56 |
| 2006/0105174 A1* | 5/2006 | Aller | .................... C08F 226/02 |
| | | | 428/411.1 |
| 2018/0065095 A1 | 3/2018 | Ardo et al. | |

FOREIGN PATENT DOCUMENTS

| CN | 108610656 | 10/2018 |
|---|---|---|
| WO | 2011023446 | 3/2011 |

OTHER PUBLICATIONS

Finkler ("Highly photostable "super"-photoacids for ultrasensitive fluorescene spectroscopy" Photochem. Photobiol. Sci. 2014, 13, p. 548-562) (Year: 2014).*

(Continued)

*Primary Examiner* — Amy C Bonaparte
(74) *Attorney, Agent, or Firm* — Wen IP LLC; Zhihua Han

(57) ABSTRACT

Disclosed are HPTS series derivatives and a synthesis method thereof, belonging to the field of organic synthesis. The HPTS series derivatives are prepared by introducing alkylamine or alcohol into sulfonic acid groups of HPTS. The synthesis method comprises the following steps: subjecting HPTS and phosphorus oxychloride to heating and reflux reaction for 12 hours under catalysis of DMF to obtain a reaction product; introducing the reaction product into ice water, stirring, precipitating solid, and performing suction filtration to obtain HPTS-$SO_2Cl$; dissolving the HPTS-$SO_2Cl$ in tetrahydrofuran to prepare solution A, and dissolving alkylamine or alcohol in tetrahydrofuran to prepare solution B; mixing the solution A with the solution B and then reacting for 24 hours at normal temperature, obtaining (Continued)

a product by rotary evaporation, and obtaining a pure compound after separation through columns. The derivatives have strong fat solubility, overcome the defect of a very strong water solubility.

7 Claims, 2 Drawing Sheets

(51) Int. Cl.
    *C07C 303/38*     (2006.01)
    *C07C 309/75*     (2006.01)
    *C07C 311/29*     (2006.01)
    *C09B 57/00*     (2006.01)

(52) U.S. Cl.
    CPC .......... *C07C 309/75* (2013.01); *C07C 311/29* (2013.01); *C07C 2603/50* (2017.05); *C09B 57/00* (2013.01)

(56) References Cited

OTHER PUBLICATIONS

Jung ("Monomolecular pyrenol-derivatives as multi-emissive probes for orthogonal reactivities" Photochem. Photobiol. Sci. 2016, 15 , p. 1544-1557) (Year: 2016).*

Phosphorus oxychloride (National Center for Biotechnology Information (2022). PubChem Compound Summary for CID 24813, Phosphorus oxychloride. Retrieved Apr. 21, 2022 from https://pubchem.ncbi.nlm.nih.gov/compound/Phosphorus-oxychloride). (Year: 2022).*

Spies. C. "Solvatochromism of Pyranine-Derived Photoacids" 1-10 Phys. Chem. Chem. Phys, Dec. 31, 2013 (Dec. 31, 2013). pp. 19894-19895. schematic diagrams 1 and 2.

* cited by examiner

HPTS SERIES DERIVATIVES AND SYNTHESIS METHOD THEREFOR

CROSS REFERENCE TO RELATED APPLICATION

This invention is a national stage application of International application number PCT/CN2018/116080, filed on Nov. 19, 2018, titled "HPTS SERIES DERIVATIVES AND SYNTHESIS METHOD THEREFOR," which claims the priority benefit of Chinese Patent Application No. 201810629427.6, filed on Jun. 19, 2018, which is hereby incorporated by reference in its entirety.

TECHNICAL FIELD

The present invention belongs to the field of organic synthesis, particularly relates to HPTS series derivatives and a method for synthesizing them.

BACKGROUND

HPTS (8-hydroxy pyrene-1,3,6-sulfonate) is a widely used green light emission-pH sensitive fluorescent dye. Depending on the pH environment, HPTS changes within protonated and deprotonated forms. Excellent properties (low toxicity, high quantum yield and large Stokes shift) make HPTS suitable for the fluorescence imaging application in human health and environment monitoring fields. However, its strong water solubility limits its application in natural environments. HPTS needs to be hydrophobic modified to avoid leaking from the probe—two-dimension fluorescent sensing foil.

Through retrieval, we found relevant applications devote to modifying HPTS to develop its application in the fluorescent sensing fields. For example, Chinese patent CN 201510171727.0 published on Nov. 24, 2017 provides a single-point dual-parameter fluorescence optical fiber sensor probe for monitoring pH value and oxygen partial pressure. This probe includes: optical fiber probe, a polyurethane hydrogel layer (fixed on optical fiber probe), pH sensitive particles, and oxygen sensitive particles (the pH sensitive particles and the oxygen sensitive particles are dispersed and embedded in the polyurethane hydrogel layer). The pH sensitive particles are prepared by covalently immobilizing HPTS on amino-modified p-HEMA; and the oxygen sensitive particles are prepared by embedding $Ru(dpp)_3^{2+}$ in organic modified silicate through solvent trichloromethane. However, the preparation process of this application is complicated.

The key step in HPTS hydrophobic modification produces sulfonyl chloride as the intermediate and acyl chloride is often used due to its high reactivity. However, acyl chloride is hardly purified by commonly used methods, residual acid chloride will be carried to the next reaction.

We also found related patents about acyl chloride preparation. For example, Chinese patent application CN200880006819.1, published on Jan. 13, 2010, discloses a method for preparing acyl chloride. The method comprises: chlorinating agent reacts with carboxylic acid in presence of catalyst. After the reaction finished, the excess chlorinating agent is removed from the reaction system, and then raw carboxylic acid (1.0-3.0 equivalent of the foregoing catalyst) is further added into the reaction system to decompose a residual Vilsmeier reagent.

Chinese patent application CN201610131176.X, published on May 18, 2016, discloses a method for preparing acyl chloride, which includes the following steps: (1) Adding carboxylic acid into reactor or dissolving carboxylic acid in organic solvent, connecting apparatuses, and raising temperature to 100-250° C. (2) Introducing phosgene into the reactor and then cooling to ambient temperature. (3) Introducing nitrogen to remove residual phosgene and hydrogen chloride. The solvent-free reaction is directly purified by distilling under reduced pressure to obtain the reaction product; solvent reaction is distilled off solvent from reaction solution.

In addition, Chinese patent application CN201310173734.5, published on Sep. 18, 2013, provides a method for preparing aromatic sulfonyl chloride derivatives, the reaction steps are as follows: (1) Introducing sulfur trioxide gas into chlorosulfonic acid to produce sulfur trichloride chlorosulfonic acid solution. Slowly adding aromatics and raising the temperature to 50-140° C. (maintaining until the reaction is completed), and then cooling to 25-35° C. (2) Controlling the temperature below 40° C., dropwise adding dilute sulfuric acid to the above reaction solution, and recovering the generated hydrogen chloride as by-product hydrochloric acid after being absorbed by water. (3) Adding solvent, stirring the mixture for 0.5-1 h, and leaving the layers to stand. The lower layer is sulfuric acid, which can be recovered as a by-product. The upper layer is distilled to remove the solvent to obtain the final product sulfonyl chloride derivative. The advantages of the invention are: stable reaction, high yield, no generation of hydrogen chloride gas in a reaction process, low energy consumption in a post-treatment process, and a high utilization value of recovered sulfuric acid.

Chinese patent application CN201510573787.5, published on Sep. 10, 2015, discloses a method for preparing aromatic sulfonyl chloride derivatives. Firstly, aromatic hydrogen derivatives are slowly added into a mixture of chlorosulfonic acid and sulfur trioxide, following by 1 or 2 drops of acetic acid, then the mixture is heated up to 50-140° C. (this temperature is constant) and reacted for 6-8 h. Subsequently, the temperature is reduced to 40-60° C., and added phosphorus oxychloride dropwise, raising the temperature to 60-120° C. for 2-4 hours. After the reaction is completed, the temperature is reduced to below 20° C., and add the reaction into ice water for dilution. Then solvent is added to distill, and the reaction product is filtered to obtain the aromatic sulfonyl chloride derivatives. The invention has stable reaction, a small demand for chlorosulfonic acid, and high product yield, avoids a problem of generation of sulfur by disproportionation reaction between phosphorus trichloride added in general reaction and sulfuric acid, generates no hydrogen chloride gas, and enables convenient post-treatment and less environmental pollution.

In summary, HPTS has low toxicity, high quantum yield and large Stokes shift, but it is urgent to develop HPTS series derivatives to overcome the shortcoming that limits its wide application in the environment.

SUMMARY

1. Problems to be Solved

In view of problems of strong water solubility of HPTS, limited application in natural environments, easy leakage of a fluorescent dye, and a narrow application range, the present invention provides HPTS series derivatives and a method for synthesizing them.

2. Technical Solution

In order to solve the foregoing problems, the technical solutions adopted by the present invention are as follows:

The present invention provides HPTS series derivatives, wherein the HPTS series derivatives are prepared by introducing alkylamine or alcohol into sulfonic acid groups of HPTS.

As a further improvement of the present invention, the alkylamine is liquid alkylamine.

As a further improvement of the present invention, the boiling point of the alcohol is below 100° C.

As a further improvement of the present invention, the alkylamine is any one of diethylamine, n-butylamine, di-n-butylamine, dimethylamine, and dipropylamine.

As a further improvement of the present invention, the alcohol is methanol or ethanol.

As a further improvement of the present invention, a method for preparing the HPTS series derivatives comprises the following steps:
(1) subjecting HPTS and phosphorus oxychloride to refluxing under catalysis of DMF to obtain the reaction product;
(2) introducing the reaction product in step (1) into ice water, stirring, precipitating, and performing suction filtration to obtain HPTS-$SO_2Cl$;
(3) dissolving the HPTS-$SO_2Cl$ in tetrahydrofuran to prepare solution A, and dissolving alkylamine or alcohol in tetrahydrofuran to prepare solution B;
(4) mixing the solution A with the solution B and then reacting at normal temperature, obtaining a product by rotary evaporation, and obtaining a pure compound after separation through columns, where in this step, the solution B is added dropwise to the solution A.

As a further improvement of the present invention, the molar ratio of the HPTS to the phosphorus oxychloride is 1:(3-4).

As a further improvement of the present invention, the molar ratio of the HPTS-$SO_2Cl$ to the alkylamine or the alcohol is 1:(3-4).

As a further improvement of the present invention, the time of the refluxing in step (1) is 12 hours; and the time of the reaction in step (4) is 24 hours.

As a further improvement of the present invention, the HPTS series derivatives are used for preparing a fluorescent sensing film.

The method for synthesizing the HPTS series derivatives comprises the following steps:
(1) subjecting HPTS and phosphorus oxychloride to refluxing under catalysis of DMF to obtain the reaction product;
(2) introducing the reaction product in step (1) into ice water, stirring, precipitating, and performing suction filtration to obtain HPTS-$SO_2Cl$;
(3) dissolving the HPTS-$SO_2Cl$ in an organic solvent with good solubility to prepare solution A, and dissolving alkylamine or alcohol in the same organic solvent with good solubility to prepare solution B; and
(4) mixing the solution A with the solution B and then reacting for 1 day at normal temperature, adding sodium bicarbonate as an acid binding agent, obtaining a product by rotary evaporation, and obtaining a pure compound after separation through columns.

As a further improvement of the present invention, the molar ratio of the HPTS to the phosphorus oxychloride is 1:(11-12).

As a further improvement of the present invention, the molar ratio of the HPTS-$SO_2Cl$ to the alkylamine or the alcohol is 1:10.

As a further improvement of the present invention, the time of the refluxing in step (1) is 12 hours; and the time of the reaction in step (4) is 24 hours.

3. Beneficial Effects

Compared with the prior art, beneficial effects of the present invention are as follows:

(1) The HPTS series derivatives of the present invention include HPTS-amide and HPTS-sulfonate. These derivatives are obtained by ligating alkylamine to an aromatic sulfonate structure of fluorescent dye HPTS which is easily soluble in water. The derivative overcomes the shortcomings of HPTS (strong water solubility, poor environmental persistence and limited application range). And using embedding agent to embed the derivative overcomes the leakage of the fluorescent dye. These improvements broaden the application scope of HPTS in fluorescent materials and pH monitoring.

(2) According to the HPTS series derivatives of the present invention, we choose HPTS to modify because it has high quantum yield and large Stokes shift. The modified HPTS series derivatives have increased hydrophobicity, and a different pKa value, which makes the HPTS series derivatives more suitable to prepare fluorescent materials to monitor pH and is easy to popularize (3) The HPTS series derivatives of the present invention are based on the modification of HPTS. These derivatives are strong fat solubility, low toxicity, and can penetrate cell membranes. Therefore, the derivatives can be used for preparing fluorescent sensing films and fluorescent probes for monitoring pH changes in cells, and have great research prospects in fluorescent materials in the fields of environment, biology, medicine, and the like.

(4) The method for synthesizing HPTS series derivatives of the present invention, the first step taking DMF as a catalyst, reacting HPTS with phosphorus oxychloride ($POCl_3$) to form HPTS-$SO_2Cl$ intermediate, and the second step reacting the HPTS-$SO_2Cl$ with alkylamine or alcohol to form HPTS-amide or HPTS-sulfonate. The HPTS-$SO_2Cl$ intermediate formed in step (1) has stable properties and can be stored in dry environment for longer time. While acyl chloride intermediate obtained by adopting a thionyl chloride reflux method in existing synthesis methods is relatively active and needs to be immediately put into the next reaction. The acyl chloride cannot be purified and stored for a long time because it is easily deteriorated. And HCl gas released by thionyl chloride reaction may corrode instruments during rotary evaporation. Therefore, the HPTS-$SO_2Cl$ intermediate formed by the synthesis method of the present invention is more suitable for synthesis of subsequent HPTS series derivatives, and acid gas is not generated in the synthesis process, thus causing no damage to experimental instruments.

(5) The method for synthesizing HPTS series derivatives of the present invention has high yield of the finally obtained HPTS series derivatives, simple synthesis steps, and mild reaction conditions, and is environmentally friendly, low in costs, and favorable for popularization.

(6) The organic solvents used in the synthesis step (3) of the present invention, which have better solubility for HPTS-$SO_2Cl$ and alkylamine or alcohol, include a mixed solution of acetone and water, tetrahydrofuran, dichloromethane, or pyridine, and the like, and the good solubility facilitates better contact reaction conditions between reactants in the next reaction.

(7) The acid binding agent is added in the synthesis step (4) of the present invention, so that by-product acid generated in the reaction process can be neutralized, moves the reaction forward; and the product obtained through this improvement step has main product points and facilitates separation on columns.

DETAILED DESCRIPTION OF EMBODIMENTS

The present invention will be further described below with reference to specific examples.

Example 1

In this example, trisodium salt of 8-hydroxy pyrene-1,3, 6-sulfonate (HPTS) is used as a precursor to synthesize 8-hydroxy-1,3,6-trisulfdiethylamine (HPTS-diethylamine), and the synthesis steps are as follows.

(1) HPTS and phosphorus oxychloride are put into reaction according to 1:3 equivalent, DMF is used as catalyst, and refluxing for 12 hours.

(2) The reaction product in step (1) is introduced into ice water at a slow speed and stirred, solid is precipitated, and suction filtration is performed to obtain HPTS-SO$_2$Cl. The yield is 90%.

(3) The HPTS-SO$_2$Cl obtained in step (2) is dissolved in an appropriate amount of tetrahydrofuran (THF) to prepare solution A with a concentration of 0.3 mmol mL$^{-1}$, and dimethylamine is dissolved in an appropriate amount of THF at 3 times equivalent to prepare solution B with a concentration of 0.5 mmol mL$^{-1}$.

(4) The solution B is added dropwise into the solution A to react for 24 hours at normal temperature, a product is obtained by rotary evaporation, and after separation on columns, a pure compound of HPTS-diethylamine can be obtained. The yield obtained in this example is 85%.

Figure 1:
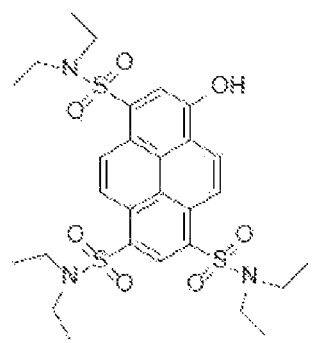
FIG. 1 is a schematic structural diagram of 8-hydroxy-1, 3,6-trisulfdiethylamine (HPTS-diethyl amine) obtained in Example 1.

FIG. 1 is a schematic structural diagram of HPTS-diethylamine obtained in this example.

The purified product of HPTS-diethylamine is detected by a Brooke 400 MHz nuclear magnetic resonance spectrometer. Measured hydrogen spectrum data is as follows:

$^1$H NMR (400 MHz, CDCl$_3$) δ 9.19 (s, 1H), 9.12 (d, J=9.9 Hz, 1H), 9.02 (d, J=9.6 Hz, 1H), 8.97 (d, J=9.8 Hz, 1H), 8.78 (d, J=9.6 Hz, 1H), 8.54 (s, 1H), 3.54-3.39 (m, 12H), 1.18 (t, J=7.1 Hz, 12H), 1.08 (t, J=7.1 Hz, 6H).

Example 2

In this example, trisodium salt of 8-hydroxy pyrene-1,3, 6-sulfonate (HPTS) is used as a precursor to synthesize HPTS-n-butylamine and a synthesis method comprises the follows steps:

(1) HPTS and phosphorus oxychloride are put into reaction according to 1:3.1 equivalent, DMF is used as catalyst, and refluxing reaction are performed for 12 hours.

(2) The reaction product in step (1) is introduced into ice water at a slow speed and stirred, solid is precipitated, and suction filtration is performed to obtain HPTS-SO2Cl. The yield is 90%.

(3) The HPTS-SO$_2$Cl obtained in step (2) is dissolved in an appropriate amount of THF to prepare solution A with a concentration of 0.3 mmol mL$^{-1}$, and n-butylamine is dissolved in an appropriate amount of THF at 3.1 times equivalent to prepare solution B with a concentration of 0.5 mmol mL$^{-1}$.

(4) The solution B is added dropwise into the solution A to react for 24 hours at normal temperature, a product is obtained by rotary evaporation, and after separation on columns, a pure compound of HPTS-n-butylamine can be obtained. The yield obtained in this example is 80%.

Figure 2:
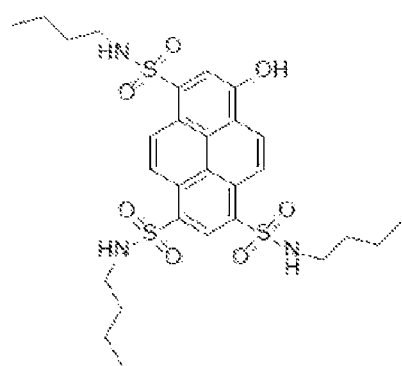
FIG. 2 is a schematic structural diagram of 8-hydroxy-1, 3,6-trisulfbutylamine (HPTS-n-butyl amine) obtained in Example 2.

FIG. 2 is a schematic structural diagram of HPTS-n-butylamine obtained in this example. The purified product of HPTS-n-butylamine is detected by a Brooke 400 MHz nuclear magnetic resonance spectrometer. Measured hydrogen spectrum data is as follows:

$^1$H NMR (400 MHz, CDCl$_3$) δ 9.29 (d, J=9.5, 7.3 Hz, 1H), δ 9.26 (d, J=9.5, 7.3 Hz, 1H), 9.20 (s, 1H), 9.13 (m, J=10.0 Hz, 4H), 8.85 (d, J=9.5 Hz, 1H), 8.46 (s, 1H), 2.63 (t, 6H), 1.54-1.30 (m, 12H), 0.89 (t, 9H).

Example 3

In this example, trisodium salt of 8-hydroxy pyrene-1,3, 6-sulfonate (HPTS) is used as a precursor to synthesize HPTS-ethyl ester and a synthesis method comprises the follows steps:

(1) HPTS and phosphorus oxychloride are put into reaction according to 1:4 equivalent, DMF is used as catalyst, and refluxing for 12 hours.

(2) The reaction product in step (1) is introduced into ice water at a slow speed and stirred, solid is precipitated, and suction filtration is performed to obtain HPTS-SO2Cl. The yield is 90%.

(3) The HPTS-SO$_2$Cl obtained in step (2) is dissolved in THF to prepare solution A with a concentration of 0.3 mmol mL$^{-1}$, and anhydrous ethanol is dissolved in THF at 4 times equivalent to prepare solution B with a concentration of 0.5 mmol mL$^{-1}$.

(4) The solution B is slowly added dropwise into the solution A to react for 24 hours at normal temperature, a product is obtained by rotary evaporation, and after separation on columns, a pure compound of HPTS-ethyl ester can be obtained. The yield of the obtained HPTS-ethyl ester is 83%.

Figure 3:
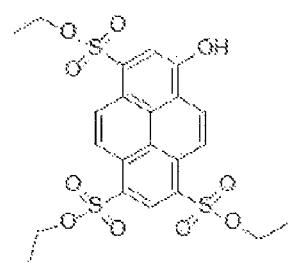
FIG. 3 is a schematic structural diagram of 8-hydroxy-1, 3,6-trisulfonic ethyl ester (HPTS-ethyl ester) obtained in Example 3.

FIG. 3 is a schematic structural diagram of HPTS-ethyl ester obtained in this example.

The purified product of HPTS-ethyl ester is detected by a Brooke 400 MHz nuclear magnetic resonance spectrometer. Measured hydrogen spectrum data is as follows:

$^1$H NMR (400 MHz, CDCl$_3$) δ 9.29 (d, J=9.5, 7.3 Hz, 1H), δ 9.26 (d, J=9.5, 7.3 Hz, 1H), 9.20 (s, 1H), 9.13 (d, J=10.0 Hz, 1H), 8.85 (d, J=9.5 Hz, 1H), 8.46 (s, 1H), 3.94 (q, 6H), 1.54 (t, 9H).

Example 4

In this example, trisodium salt of 8-hydroxy pyrene-1,3,6-sulfonate (HPTS) is used as a precursor to synthesize HPTS-di-n-propyl amine and a synthesis method comprises the follows steps:

(1) HPTS and phosphorus oxychloride are put into reaction according to 1:3.1 equivalent, DMF is used as catalyst, and refluxing for 12 h.

(2) The reaction product in step (1) is introduced into ice water at a slow speed and stirred, solid is precipitated, and suction filtration is performed to obtain HPTS-S02C1. The yield is 90%.

(3) The HPTS-SO$_2$Cl obtained in step (2) is dissolved in an appropriate amount of THF to prepare solution A with a concentration of 0.3 mmol mL$^{-1}$, and di-n-propyl amine is dissolved in an appropriate amount of THF at 3.1 times equivalent to prepare solution B with a concentration of 0.5 mmol mL$^{-1}$.

(4) The solution B is slowly added dropwise into the solution A to react for 24 hours at normal temperature, a product is obtained by rotary evaporation, and after separation on columns, a pure compound of HPTS-di-n-propyl amine can be obtained. The yield obtained in this example is 75%.

Figure 4:
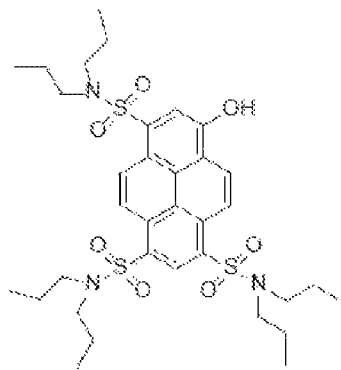
FIG. 4 is a schematic structural diagram of 8-hydroxy-1, 3,6-trisulfdipropylamine (HPTS-di-n-propylamine) obtained in Example 4.

FIG. 4 is a schematic structural diagram of HPTS-di-n-propyl amine obtained in this example.

The purified product of HPTS-di-n-propyl amine is detected by a Brooke 400 MHz nuclear magnetic resonance spectrometer. Measured hydrogen spectrum data is as follows:

$^1$H NMR (400 MHz, CDCl$_3$) δ 9.19 (s, 1H), 9.12 (d, J=9.9 Hz, 1H), 9.02 (d, J=9.6 Hz, 1H), 8.97 (d, J=9.8 Hz, 1H), 8.78 (d, J=9.6 Hz, 1H), 8.54 (s, 1H), 3.54-3.39 (m, 12H), 1.08 (m, J=7.1 Hz, 12H), 0.98 (t, J=7.1 Hz, 18H).

Example 5

In this example, trisodium salt of 8-hydroxy pyrene-1,3,6-sulfonate (HPTS) is used as a precursor to prepare HPTS-dibutylamine and a preparation method comprises the follows steps:

(1) HPTS and phosphorus oxychloride are put into reaction according to 1:3.1 equivalent, DMF is used as catalyst, and refluxing for 12 hours.

(2) The reaction product in step (1) is introduced into ice water at a slow speed and stirred, solid is precipitated, and suction filtration is performed to obtain HPTS-S02C1. The yield is 90%.

(3) The HPTS-SO$_2$Cl obtained in step (2) is dissolved in an appropriate amount of THF to prepare solution A with a concentration of 0.3 mmol mL$^{-1}$, and di-n-butylamine is dissolved in an appropriate amount of THF at 3.1 times equivalent to prepare solution B with a concentration of 0.5 mmol mL$^{-1}$.

(4) The solution B is slowly added dropwise into the solution A to react for 24 hours at normal temperature, a product is obtained by rotary evaporation, and after separation on columns, a pure compound of HPTS-di-n-butylamine can be obtained. The yield obtained in this example is 69%.

Figure 5:
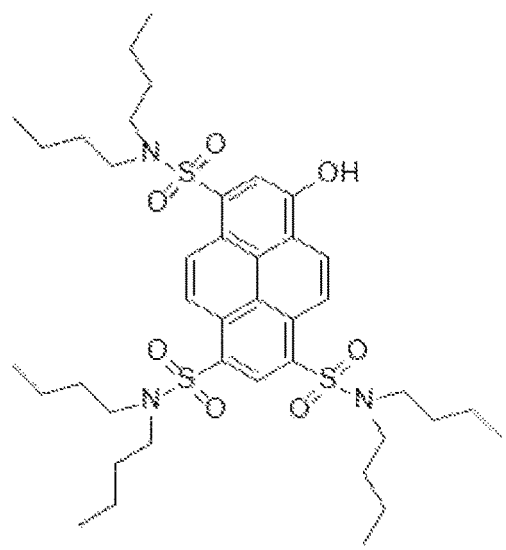
FIG. 5 is a schematic structural diagram of 8-hydroxy-1, 3,6-trisulfdibutylamine (HPTS-di-n-butylamine) obtained in Example 5.

FIG. 5 is a schematic structural diagram of HPTS-di-n-butylamine obtained in this example.

The purified product of HPTS-di-n-butylamine is detected by a Brooke 400 MHz nuclear magnetic resonance spectrometer. Measured hydrogen spectrum data is as follows:

$^1$H NMR (400 MHz, CDCl$_3$) δ 9.19 (s, 1H), 9.12 (d, J=9.9 Hz, 1H), 9.02 (d, J=9.6 Hz, 1H), 8.97 (d, J=9.8 Hz, 1H), 8.78 (d, J=9.6 Hz, 1H), 8.54 (s, 1H), 3.54-3.39 (m, 12H), 1.40-1.21 (m, J=7.1 Hz, 24H), 0.98 (t, J=7.1 Hz, 18H).

Example 6

In this example, trisodium salt of 8-hydroxy pyrene-1,3,6-sulfonate (HPTS) is used as a precursor to prepare HPTS-methyl ester and a preparation method comprises the follows steps:

(1) HPTS and phosphorus oxychloride are put into reaction according to 1:3.1 equivalent, DMF is used as catalyst, and refluxing for 12 hours.

(2) The reaction product in step (1) is introduced into ice water at a slow speed and stirred, solid is precipitated, and suction filtration is performed to obtain HPTS-S02C1. The yield is 90%.

(3) The HPTS-SO$_2$Cl obtained in step (2) is dissolved in an appropriate amount of THF to prepare solution A with a concentration of 0.3 mmol mL$^{-1}$, and methanol is dissolved in an appropriate amount of THF at 3.1 times equivalent to prepare solution B with a concentration of 0.5 mmol mL$^{-1}$.

(4) The solution B is slowly added dropwise into the solution A to react for 24 hours at normal temperature, a product is obtained by rotary evaporation, and after separation on columns, a pure compound of HPTS-methyl ester can be obtained. The yield obtained in this example is 89%.

Figure 6:
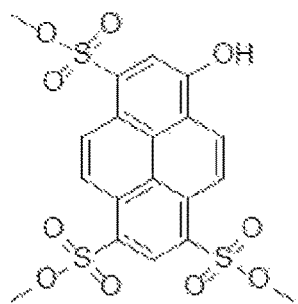
FIG. 6 is a schematic structural diagram of 8-hydroxy-1, 3,6-trisulfonic methyl ester (HPTS-methyl ester) obtained in Example 6.

FIG. 6 is a schematic structural diagram of HPTS-methyl ester obtained in this example.

The purified product of HPTS-methyl ester is detected by a Brooke 400 MHz nuclear magnetic resonance spectrometer. Measured hydrogen spectrum data is as follows:

$^1$H NMR (400 MHz, CDCl$_3$) δ 9.29 (d, J=9.5, 7.3 Hz, 1H), δ 9.26 (d, J=9.5, 7.3 Hz, 1H), 9.20 (s, 1H), 9.13 (d, J=10.0 Hz, 1H), 8.85 (d, J=9.5 Hz, 1H), 8.46 (s, 1H), 3.94 (q, 6H), 1.54 (t, 9H).

Figure 7:
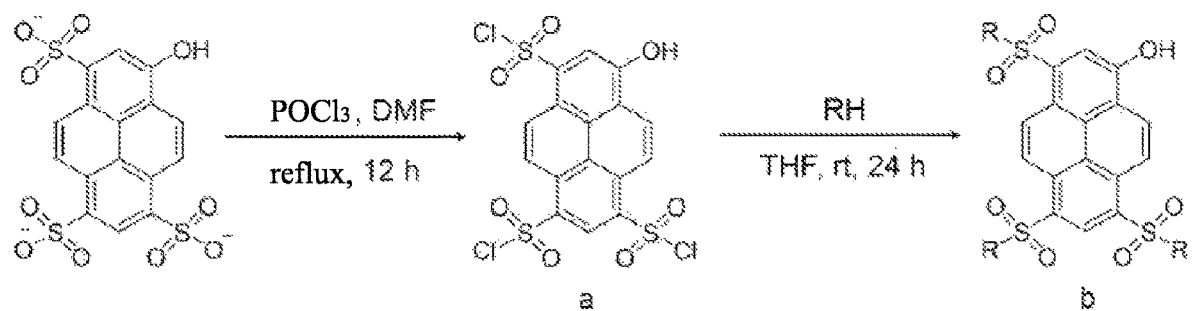
FIG. 7 is a schematic diagram of a reaction synthesis route of HPTS series derivatives of the present invention.

FIG. 7 is a schematic diagram of a reaction synthesis route of HPTS series derivatives of the present invention. As shown in FIG. 7, the reaction uses trisodium salt of 8-hydroxy pyrene-1,3,6-sulfonate (HPTS) as a precursor to prepare HPTS-amide or HPTS-sulfonate. Firstly, DMF is used as catalyst, HPTS is reacted with POCl$_3$ to form HPTS-SO$_2$Cl, and then HPTS-SO$_2$Cl is reacted with alkylamine or alcohol to form HPTS-amide or HPTS-sulfonate.

What needs to be explained above is that there is no obvious difference in yields of derivatives obtained by using different synthesis routes. Main influence of different solvents in a process of preparing different derivatives lies in whether main product points are clear upon thin layer chromatography analysis, which facilitates separation through columns. Adjustment and screening can be performed according to experimental requirements.

The present invention and its implementations have been schematically described above, and the description is not limited. What is shown in the accompanying drawings is only one of the embodiments of the present invention, and an actual process is not limited thereto. Therefore, if a person of ordinary skill in the art designs similar structural modes and examples without creative efforts in an enlightenment without departing from the creation purpose of the present invention, the structural modes and the examples should fall within the protection scope of the present invention.

DRAWINGS OF THE SPECIFICATION

Disclosed are HPTS series derivatives and a synthesis method thereof, belonging to the field of organic synthesis. The HPTS series derivatives are prepared by introducing alkylamine or alcohol into sulfonic acid groups of HPTS. The synthesis method comprises the following steps: subjecting HPTS and phosphorus oxychloride to heating and reflux reaction for 12 hours under catalysis of DMF to obtain a reaction product; introducing the reaction product into ice water, stirring, precipitating solid, and performing suction filtration to obtain HPTS-$SO_2$Cl; dissolving the HPTS-$SO_2$Cl in tetrahydrofuran to prepare solution A, and dissolving alkylamine or alcohol in tetrahydrofuran to prepare solution B; mixing the solution A with the solution B and then reacting for 24 hours at normal temperature, obtaining a product by rotary evaporation, and obtaining a pure compound after separation through columns. The derivatives have strong fat solubility, overcome the defect of a very strong water solubility.

What is claimed is:

1. A method for synthesizing a 8-hydroxy pyrene-1,3,6-sulfonate (HPTS) series derivative by introducing an alkylamine or an alcohol into sulfonic acid groups of the HPTS, comprising the following steps:
   (1) subjecting HPTS and phosphorus oxychloride to refluxing under catalysis of DMF to obtain a reaction product;
   (2) introducing the reaction product of step (1) into ice water, stirring, precipitating, and performing suction filtration to obtain HPTS-$SO_2$Cl;
   (3) dissolving the HPTS-$SO_2$Cl in tetrahydrofuran to prepare solution A, and dissolving an alkylamine or an alcohol in tetrahydrofuran to prepare solution B; and
   (4) mixing the solution A with the solution B and then reacting at normal temperature, obtaining a product by rotary evaporation, and obtaining a pure compound after separation through columns.

2. The method for synthesizing the HPTS series derivatives according to claim 1, wherein the molar ratio of the HPTS to the phosphorus oxychloride is 1:3-4.

3. The method for synthesizing the HPTS series derivatives according to claim 1, wherein the molar ratio of the HPTS-$SO_2$Cl to the alkylamine or the alcohol is 1:3-4.

4. The method for synthesizing the HPTS series derivatives according to claim 3, wherein the time of the refluxing in step (1) is 12 hours; and the time of the reaction in step (4) is 24 hours.

5. A method for synthesizing a 8-hydroxy pyrene-1,3,6-sulfonate (HPTS) series derivative by introducing an alkylamine or an alcohol into sulfonic acid groups of the HPTS, comprising the following steps:
   (1) subjecting HPTS and phosphorus oxychloride to refluxing under catalysis of DMF to obtain a reaction product;
   (2) introducing the reaction product in step (1) into ice water, stirring, precipitating, and performing suction filtration to obtain HPTS-$SO_2$Cl;
   (3) dissolving the HPTS-$SO_2$Cl in an organic solvent to prepare solution A, and dissolving alkylamine or alcohol in an organic solvent to prepare solution B; and
   (4) mixing the solution A with the solution B and then reacting for 1 day at normal temperature, adding sodium bicarbonate as an acid binding agent, obtaining a product by rotary evaporation, and obtaining a pure compound after separation through columns.

6. The method for synthesizing the HPTS series derivatives according to claim 2, wherein the molar ratio of the HPTS-$SO_2$Cl to the alkylamine or the alcohol is 1:3-4.

7. The method for synthesizing the HPTS series derivatives according to claim 6, wherein the time of the refluxing in step (1) is 12 hours; and the time of the reaction in step (4) is 24 hours.

* * * * *